United States Patent [19]

Schmaier et al.

[11] Patent Number: 5,472,945
[45] Date of Patent: Dec. 5, 1995

[54] MODULATION OF BLOOD PRESSURE AND INHIBITION OF PLATELET ACTIVATION WITH KININOGEN FRAGMENT

[75] Inventors: Alvin H. Schmaier, Ann Arbor; Yongping Jiang, Northville, both of Mich.

[73] Assignee: Temple University- of the Commonwealth System of Higher Education, Philadelphia, Pa.

[21] Appl. No.: 193,114

[22] PCT Filed: Aug. 13, 1992

[86] PCT No.: PCT/US92/06809

§ 371 Date: Feb. 9, 1994

§ 102(e) Date: Feb. 9, 1994

Related U.S. Application Data

[63] Continuation-in-part of Ser. No. 744,545, Aug. 13, 1991, abandoned.

[51] Int. Cl.[6] .............................. A61K 38/17; C07K 14/47
[52] U.S. Cl. .............................. 514/12; 514/21; 530/380
[58] Field of Search .................... 514/12, 13, 21; 530/314, 350, 380, 386; 930/250, DIG. 600, DIG. 601

[56] References Cited

U.S. PATENT DOCUMENTS

| | | | |
|---|---|---|---|
| 3,862,114 | 1/1975 | Scandrett | 530/331 |
| 4,378,346 | 3/1983 | Tankersky | 530/364 |
| 4,638,047 | 1/1987 | Szelke et al. | 530/332 |
| 4,908,431 | 3/1990 | Colman et al. | 530/809 |
| 5,037,957 | 8/1991 | Grubb et al. | 530/331 |

OTHER PUBLICATIONS

Cell, vol. 50, issued 28 Aug. 1987, Reeck et al, "Homology in Proteins and Nucleic Acids . . . ", p. 667.
Eur. J. Biochem., vol. 142, issued 1984, Lottspeich et al, "Human Low–Molecular–Mass Kininogen", pp. 227–232.
Jiang et al., *The Journal of Biological Chemistry*, vol. 267, No. 8, pp. 3712–3717 (Feb. 1992).
Van Iwaarden et al., *The Journal of Biological Chemistry*, vol. 263, No. 10, pp. 4698–4703 (Apr. 1988).
Kellermann et al., *European Journal of Biochemistry* 154, 471–478 (1986).
Müller–Esterl, *Atemw.–Lungenkrkh.*, Jahrg. 14, 1. Suppl. 511–522 (1988).
Vogel et al., *The Journal of Biological Chemistry*, vol. 263, No. 25, pp. 12661–12668 (Sep. 1988).
Salvesen et al., *Biochem. J.*, 234, 429–434 (1986).
Gustafson et al., *J. Clin. Invest.*, 78, 310–318 (Jul. 1986).
Gustafson et al., *J. Clin. Invest.*, 84, 28–35 (Jul. 1989).
Greengard et al., *Biochemistry*, 23, 6863–6869 (1984).
Meloni et al., *The Journal of Biological Chemistry*, 266, No. 11, 6786–6794 (1991).
Neely et al., *Blood* 72: (Suppol.) 304a (1988) Abs.
Gustafson et al., *Clinical Research* 34, No. 2 459A (1986) (Abs.).
Meloni et al., *Circulation* 78: (Suppl.) II–545 (1988) (Abs.).
Schmaier et al., *J. Biol. Chem.* 263, 16327–16333 (1988).
Kuna et al., *Blood* 76: (Suppl.) 426a (1990) (Abs.).

*Primary Examiner*—Jeffrey E. Russel
*Attorney, Agent, or Firm*—Seidel Gonda Lavorgna & Monaco

[57] ABSTRACT

The release of bradykinin into the circulatory system is potentiated by administration of a polypeptide having an amino acid sequence corresponding to domain 3 of the human kininogen heavy chain. The polypeptide competitively inhibits the binding of high and low molecular weight kininogen to platelets and other cells which protect the kininogens from kallikrein cleavage, thereby increasing the level of bradykinin in the cirulation. The resulting in vivo effect is an intravascular elevation of bradykinin and concomitant lowering of blood pressure. The domain 3 polypeptide also inhibits thrombin-induced platelet and endothelial cell activation.

18 Claims, 8 Drawing Sheets

FIG. 1

| | | | | | | | | | | | | | | |
|---|---|---|---|---|---|---|---|---|---|---|---|---|---|---|
|Cys|Val|Gly|Cys|Pro<br>5|Arg|Asp|Ile|Pro|Thr<br>10|Asn|Ser|Pro|Glu|Leu<br>15|
|Glu|Glu|Thr|Leu|Thr<br>20|His|Thr|Ile|Thr|Lys<br>25|Leu|Asn|Ala|Glu|Asn<br>30|
|Asn|Ala|Thr|Phe|Tyr<br>35|Phe|Lys|Ile|Asp|Asn<br>40|Val|Lys|Lys|Ala|Arg<br>45|
|Val|Gln|Val|Val|Ala<br>50|Gly|Lys|Lys|Tyr|Phe<br>55|Ile|Asp|Phe|Val|Ala<br>60|
|Arg|Glu|Thr|Thr|Cys<br>65|Ser|Lys|Glu|Ser|Asn<br>70|Glu|Glu|Leu|Thr|Glu<br>75|
|Ser|Cys|Glu|Thr|Lys<br>80|Lys|Leu|Gly|Gln|Ser<br>85|Leu|Asp|Cys|Asn|Ala<br>90|
|Glu|Val|Tyr|Val|Val<br>95|Pro|Trp|Glu|Lys|Lys<br>100|Ile|Tyr|Pro|Thr|Val<br>105|
|Asn|Cys|Gln|Pro|Leu<br>110|Gly|Met|Ile|Ser|Leu<br>115|Met|Lys| | | |

MODULATION OF BLOOD PRESSURE AND INHIBITION OF PLATELET ACTIVATION WITH KININOGEN FRAGMENT

CROSS REFERENCE TO RELATED APPLICATION

This is a continuation-in-part of application Ser. No. 07/744,545 filed Aug. 13, 1991, now abandoned.

FIELD OF THE INVENTION

This invention relates to the modulation of blood pressure and the management of hypertension by manipulating the extent and location of bradykinin availability in the circulatory system. The invention also relates to the inhibition of thrombin-induced platelet and endothelial cell activation.

BACKGROUND OF THE INVENTION

The kininogens are single-chain glycoproteins which are present in human blood plasma and tissues in two forms: high molecular weight kininogen (120 kDa) and low molecular weight kininogen (64 kDa). A single gene controls the synthesis of both kininogens (Takagaki et al., *J. Biol. Chem.* 266, 6786 (1985)). The difference between the high molecular weight form and the low molecular weight form is the addition of a unique 56 kDa light chain on high molecular weight kininogen by an alternative mRNA splicing of the single kininogen gene (Kitamura et al., *J. Biol. Chem.* 260, 8610 (1985); Kakizuka et al., *J. Biol. Chem.* 265, 10102 (1990)). The presence of the 56 kDa light chain on high molecular weight kininogen gives this form of kininogen unique antigenic and functional properties. The plasma concentration of high molecular weight kininogen is 0.67 micromolar, while the plasma concentration of low molecular weight kininogen is 2.4 micromolar.

There are numerous functions for the plasma kininogens which follow from their structure. The first function of both kininogens is that they serve as the parent proteins for the nonapeptide bradykinin, and for the decapeptide lys-bradykinin. These kinins are the most potent, naturally-occurring vasodilitory mediators. They have profound effects on endothelium, stimulating their prostaglandin synthetic pathways and stimulating release of plasminogen activators. Bradykinin and its derivatives may be major local modulators of the autocrine regulation of blood pressure. Bradykinin is best liberated from high molecular weight kininogen by plasma kallikrein, activated factor XII, factor XIa and plasmin. Low molecular weight kininogen is a better substrate for tissue kallikreins liberating lysbradykinin. Elastase treatment of low molecular weight kininogen makes it a better substrate for kinin release by plasma kallikrein.

Both low and high molecular weight kininogens have identical amino acid sequences from their N-terminus through 12 amino acids beyond the carboxy-terminus of bradykinin. Their so-called "heavy chains" from the amino-terminus of the protein to the amino-terminal end of bradykinin are identical. These heavy chains have been characterized to have three domains (domains 1–3). Domains 2 and 3 contain the amino acid sequence Gln-Val-Val-Ala-Gly (SEQ ID NO:2). This amino acid sequence is highly conserved in evolution in cysteine protease inhibitors (Ohkubo et al., *Biochem.* 23, 3891 (1984)). Domain 2 uniquely appears to be a good inhibitor of calpains, which are calcium-dependent tissue cysteine proteases (Schmaier et al, *J. Clin. Invest.* 77, 1565 (1986)). The kininogens' ability to inhibit calpains may have some function in preventing calpain-induced platelet aggregation after thrombin activation (Schmaier et al., *Blood* 75, 1273 (1990)). Domain 4 on both high and low molecular weight kininogen comprises bradykinin.

High molecular weight kininogen also functions as a cofactor for the activation of the following plasma zymogens: factor XII, prekallikrein, and factor XI. These three plasma zymogens when activated to enzymes, along with high molecular weight kininogen, comprise the proteins of the contact phase of plasma proteolysis. In addition to being a cofactor for activation of each of these plasma zymogens, high molecular weight kininogen is also a substrate of each of their proteolytic forms. The procofactor activity of high molecular weight kininogen is based upon two areas on its unique 56 kDa light chain: First, high molecular weight kininogen has a region on domain 5 which is rich in the basic amino acids glycine, histidine, and lysine that has the ability to bind to anionic surfaces such as kaolin. Secondly, high molecular weight kininogen has a region on its domain 6 which serves as the binding region for prekallikrein and factor XI. Interference with high molecular weight kininogen's ability to bind to negatively charged surfaces with a monoclonal antibody, such as C11C1 (ATCC HB-8964) blocks its procofactor or procoagulant activity (Schmaier et al., *J. Biol. Chem.* 262, 1405 (1987); U.S. Pat. No. 4,908,431). Similarly, interference with high molecular weight kininogen's ability to bind prekallikrein and/or factor XI by a monoclonal antibody directed to its prekallikrein/factor IX binding region also interfers with its procoagulant activity (Tait et al., *J. Biol. Chem.* 261, 15396 (1986); Vogel et al., *J. Biol. Chem.* 265, 12494 (1990)).

It has been a common thought in the contact field that since high molecular weight kininogen has a specific region on its unique light chain that binds to artificial, negatively-charged surfaces, then if this protein interacts with biologic surfaces, e.g., cell membranes, that it does so through the surface binding region contained on domain 5 of its unique 56 kDa light chain. High molecular weight kininogen has been shown to have specific, reversible and saturable binding sites on unstimulated platelets (Gustafson et al., *J. Clin. Invest.*, 78, 310 (1986)), activated platelets (Greengard et al, *Biochemistry* 23, 6863 (1984)), granulocytes (Gustafson et al., *J. Clin. Invest.*, 84, 28 (1989)), and human umbilical vein endothelial cells (Van Iwaarden et al., 263, 16327 (1988)). The affinity for high molecular weight kininogen to bind to cells in the vascular compartment is between 0.015 and 0.05 micromolar. Since the plasma high molecular weight kininogen concentration is 0.67 micromolar, all intravascular kininogen binding sites should be saturated in vivo. However, the common thought that there could only be a cell-binding region on the light chain of high molecular weight kininogen was shown to be incorrect by the publication that low molecular weight kininogen, the other kininogen which does not contain the 56 kDa light chain that has procoagulant activity, could also specifically, reversibly and saturably bind to human platelets (Meloni et al., *J. Biol. Chem.* 266, 6786 (1991)). Low molecular weight kininogen's ability to bind to platelets inhibited or was inhibited by high molecular weight kininogen.

Unrelated to the foregoing discussion of the kininogens, treatment of hypertension has consisted of therapy aimed at influencing a number of components involved in blood pressure regulation. β-Adrenergic blockers have been used to decrease hypertension by limiting the extent of cardiac output. α-Adrenergic antagonists, e.g., α-methyl dopa, have been utilized to stimulate dilation of arteries. Yet another antihypertensive therapy utilizes nitrate compounds, e.g., nitropaste, to produce venous pooling and arterial dilitation by other means. Finally, inhibitors of kininases, such as captopril, have been used to inhibit one of the seven enzymes that degrade physiologically produced bradykinin. The result is a potentiation of bradykinin's effect by limiting its rate of degradation. None of these standard antihypertensive therapies involves the direct elevation of intravascular bradykinin.

Hereinafter, "human kininogen" shall mean, unless otherwise indicated, both high and low molecular weight forms of any kininogen molecule, in all its various forms derived from human plasma, platelets, endothelial cells, granulocytes, or skin or other tissues or organs, regardless of whether it is found in the fluid or the tissue phase.

"HK" shall mean human high molecular weight kininogen.

"LK" shall mean human low molecular weight kininogen, also known as α-cysteine protease inhibitor, or $\alpha^{\pm}$-thiol protease inhibitor, or $\alpha_2$-thiol protease inhibitor.

"Light chain" shall mean, when referring or relating to human kininogen, the 56 kDa intermediate plasma kallikrein-cleavage fragment of HK which has the ability to correct the coagulant defect in total kininogen-deficient plasma.

"Heavy chain" shall mean, when referring or relating to human kininogen, the 64 kDa kallikrein-cleavage fragment of HK or LK, which is free of bradykinin and "light chain".

"D3" or "domain 3" with respect to the kininogen heavy chain shall mean the trypsin-cleavage fragment of the human kininogen heavy chain which is about 21 kDa.

The term "homology" means the degree of identity between two amino acid sequences. For example, 80% homology with respect to a 100-amino acid native polypeptide means that a homologous polypeptide contains identical amino acids when compared to the native polypeptide in any 80 positions out of the 100 amino acid positions of the native polypeptide. By way of further examples, an 80% homologous polypeptide may be generated by any of the following modifications: (i) removing a twenty amino acid sequence from the amino or carboxy terminus of the 100-amino acid native sequence either as a continuous 20-amino acid deletion, or by deleting 20 noncontinuous amino acid residues; (ii) inserting as an internal insertion 20 amino acids into the native 100-amino acid native sequence, either as a continuous 20-amino acid insert, or in isolated inserts comprising one or more amino acids; (iii) adding up to 20 amino acids as an amino- or carboxy terminus of the native sequence; or (iv) any combination of one or more of the aforesaid modifications, the result of which is a homologous sequence of amino acids identical to the native sequence in at least 80 out of 100 positions.

SUMMARY OF THE INVENTION

A method of increasing vascular bradykinin release comprises administering to an individual an effective amount of a polypeptide which inhibits the cell binding of human kininogen. The polypeptide consists essentially of an amino acid sequence corresponding to the about 21 kDa native trypsin-cleavage fragment of human kininogen heavy chain, or analog or fragment of the native fragment which inhibits cell binding of kininogen. Preferably, the amino acid sequence of the polypeptide has at least 50% homology with the native sequence of domain 3. More preferably, the amino acid sequence of the polypeptide has at least 80%, most preferably at least 90%, homology with the domain 3 native sequence.

The invention also comprises a method for lowering blood pressure comprising administering to an individual in need of such treatment, an effective amount of the aforesaid polypeptide.

The invention yet further comprises a method of inhibiting thrombin-induced platelet or other cell activation, comprising administering to an individual in need of such treatment, an effective amount of the aforesaid polypeptide.

The invention also comprises therapeutic compositions comprising a pharmaceutically acceptable carrier and a polypeptide consisting essentially of the about 21 kDa native trypsin-cleavage fragment of human kininogen heavy chain, or analog or fragment of said native fragment, which analog or fragment inhibits the binding of kininogen and/or thrombin to cells, particularly binding to platelets and endothelial cells.

DESCRIPTION OF THE FIGURES

FIG. 3 is a study of direct $^{125}$I-D3 binding to platelets. Gel-filtered platelets ($2.0\times10^8$/ml) in Hepes-Tyrode's buffer were incubated for 5 to 90 min. at 37° C. with $^{125}$I-D3 (30 nM) in the presence of 50 μM $Zn^{2+}$ without any competitor (●). At each time point, samples were removed and the bound $^{125}$I-D3 was separated from unbound $^{125}$I-D3 by centrifugation through an oil gradient. Nonspecific binding was measured concommitantly using replicate incubants containing a 35-fold molar excess of unlabeled D3 (o) or 200-fold molar excess HK (□) in the presence of 50 μM zinc. The data plotted are the mean of three experiments.

FIG. 4 is an inhibition binding study of $^{125}$I-D3 binding to platelets by unlabelled D3. $^{125}$I-D3 was incubated with washed platelets in Hepes-Tyrode's buffer containing 50 μM $Zn^{2+}$ for 20 min. at 37° C. in the presence of increasing concentrations of unlabelled D3. The graph depicts percent specific binding of $^{125}$I-D3 on the ordinate. The abscissa represents the concentration of the unlabelled D3. Each point in the Figure represents the mean ±SD of the values from three identical experiments.

FIG. 5A: specific binding (▲) was calculated by subtracting nonspecific binding (□) (determined by adding a 35-fold molar excess unlabelled D3) from total binding (Δ). FIG. 5B: the specific binding data from FIG. 5A were graphed on a bound/free versus bound plot according to the method of Scatchard, Ann. N.Y. Acad. Sci. 51, 660 (1949). The data presented in these Figures are from one representative experiment of four.

FIG. 7 is a plot of D3 inhibition of $^{125}$I-thrombin to platelets. Gel-filtered platelets in Hepes-Tyrode's buffer containing 50 µM $ZnCl_2$ and 2 mM $CaCl_2$ were incubated for 5–120 min. at 37° C. with 1 nM $^{125}$I-α-thrombin (IIa) alone (□) or in the presence of 200 nM HK (●) or 200 nM D3 (○). The data plotted are the mean of two independent experiments.

FIG. 8 is a light transmittance tracing showing the inhibition of thrombin-induced platelet activation by HK and D3 compared to a control (no polypeptide). Gel-filtered platelets ($2.0 \times 10^8$/ml) in Hepes-Tyrode's buffer were treated with 1 µM HK or D3 immediately before the introduction of the agonist, human α-thrombin (0.125 U/ml). The instant of agonist introduction is indicated by the arrows. The platelet aggregation was measured for 5 min. after the introduction of the agonist. Control platelets received an identical volume of buffer. The figure is a representative experiment of three experiments performed with different platelet donors and different batches of HK and D3 which were dialyzed to remove any trace of inhibitors necessary in their preparation.

DETAILED DESCRIPTION OF THE INVENTION

The rate of plasma and tissue kallikrein cleavage of HK is affected by its binding to cells. Platelet-bound HK has a slower rate of cleavage by plasma and tissue kallikrein than kininogen in solution. The rate of cleavage of cell-bound kininogen by kallikreins directly correlates with the rate of bradykinin liberation. Bradykinin liberation is depressed when kininogens are bound to cells and thus protected from kallikrein cleavage.

According to the present invention, domain 3 from kininogen heavy chain has been recognized to inhibit HK and LK from binding to platelets and other cells, such as human umbilical vein endothelial cells. Blocking HK and LK from binding to cell membranes increases the level of free HK and LK in the circulation. Since soluble kininogens are more susceptible than cell-bound kininogen to kallikrein cleavage and kinin liberation, more kinin is liberated at a faster rate. The resulting in vivo effect is an intravascular elevation of bradykinin with resultant influence in endothelial function and a lowering of blood pressure.

Modulation of kininogen binding to cells by administration of a polypeptide corresponding to domain 3, and the attendant increase in bradykinin delivery, comprises a new therapy for hypertension. Infusion of the specific cell binding domain on the heavy chain of the kininogens will decrease the extent of cell-bound, intact kininogen in vivo and thus allow for more soluble kininogen to be susceptible for kallikrein cleavage and kinin liberation. Since kinin liberation from soluble kininogen occurs faster than cleavage of cell-bound kininogen, the increased bradykinin will result in a lowering of physiologic blood pressure in vivo. The human kininogen binding domain, which is naturally occurring and would not be immunogenic in humans, is thus a useful agent to decrease blood pressure in the various clinical situations such as malignant or essential hypertension.

It has also been found that domain 3 inhibits thrombin binding to cells, particularly cells of the vascular compartment involved in the inflammatory response, such as platelets and endothelial cells. Thus, we have found that domain 3 has the ability to inhibit thrombin-induced platelet activation by blocking thrombin from binding to platelets. Administration of a polypeptide corresponding to domain 3 comprises a therapeutic method for inhibiting thrombin-induced activation of platelets and endothelial cells.

Inhibition of platelet activation by domain 3 is observed by a marked decrease in the platelet's ability to aggregate and secrete their granule contents. The granule contents comprise proteins which participate in hemostasis, thrombosis and the inflammatory response. Inhibition of endothelial cell activation may similarly be observed by a decrease in secretion of endothelial cell contents such as tissue plasminogen activator and von Willebrand factor.

Since the domain 3 polypeptide functions to inhibit cell activation by blocking thrombin binding to its target cells, the polypeptide is a selective inhibitor of thrombin-induced platelet activation. Administration of D3 therefore does not impact on induction of platelet activation by physiological substances other than thrombin, such as, for example collagen, adenosine diphosphate, epinephrine and platelet activating factor.

Figure 1:
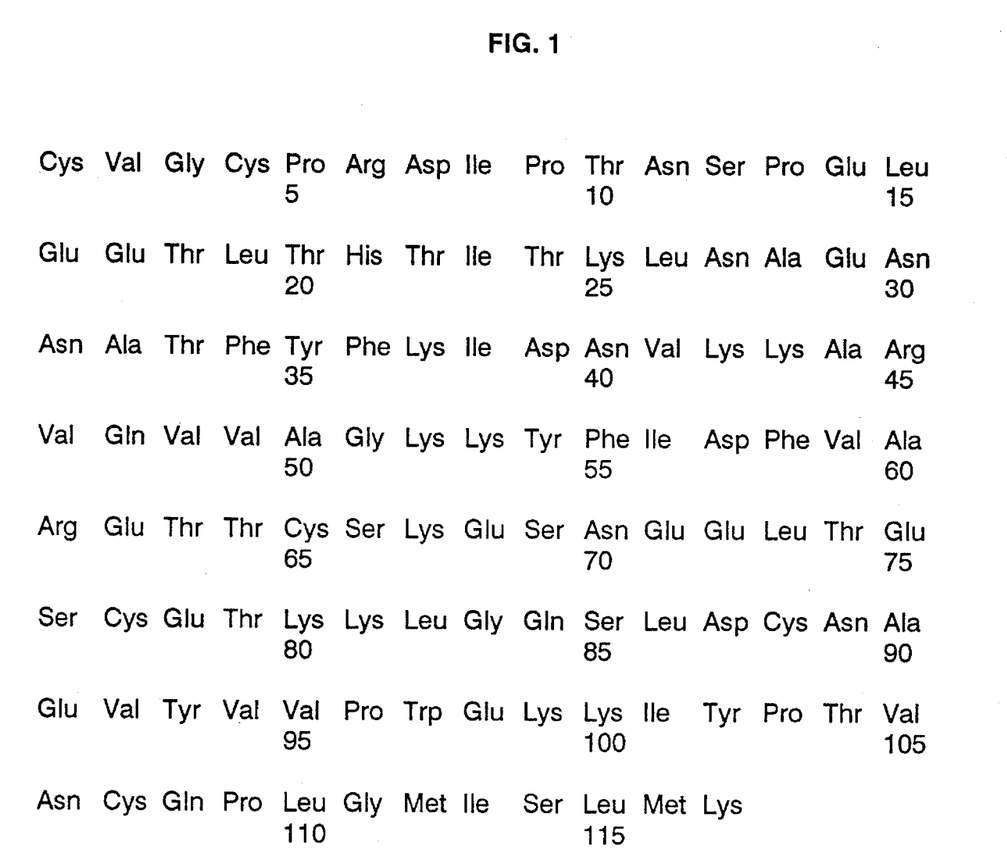
FIG. 1 comprises the native amino acid sequence of domain 3 (SEQ ID NO: 1).

The amino acid sequence of the human kininogen heavy chain is known. See, for example, Salveson et al., *Biochem. J.* 234, 429–434 (1986); Kellerman et al., *Eur. J. Biochem.* 154, 471–478 (1986). Domain 3 thereof is generally regarded as comprising about residues 246–362 of the mature human kininogen heavy chain polypeptide. The native domain 3 amino acid sequence is contained in FIG. 1 (SEQ ID NO:1). The numbering in the Figure begins with "1" from the first residue of domain 3. The mature polypeptide is generated by a post-translational modification which cleaves an 18-amino acid leader from the translated polypeptide.

Domain 3 may be prepared from human plasma as described in detail hereinafter. Total kininogen is purified from plasma by affinity chromatography over, for example, CM-papain SEPHAROSE 2B. LK is separated from HK by adsorption with a reagent which selectively adsorbs HK and not LK. For example, any reagent comprising an ionic surface capable of binding HK through domain 5 may be utilized. The remaining purified LK is then cleaved into two fragments by trypsin cleavage. Trypsin cleaves LK for the most part between amino acids 245 and 246 in the kininogen heavy chain, according to the numbering of the mature polypeptide. Some variation in the location of the cleavage site is apparent. The smaller 21 kDa trypsin-cleavage fragment which comprises domain 3, is separated from the larger 44 kDa fragment by gel filtration.

While domain 3 is most advantageously prepared from LK, however, HK may alternatively comprise the starting material for obtaining the domain 3 polypeptide, provided HK is first cleaved by plasma or tissue kallikrein and then reduced and alkylated to release the 56 kDa light chain, leaving the 64 kDa heavy chain for trypsin cleavage. Alternatively, domain 3 may be prepared by recombinant DNA techniques. Based upon the known amino acid sequence of domain 3, a synthetic gene may be constructed corresponding to that sequence, and introduced into an appropriate host by appropriate cloning vectors. Thus, it should be understood that the present invention is not merely limited to the use of domain 3 as isolated by the enzymatic cleavage and chromatographic processes described herein, but also includes the corresponding polypeptide prepared by recombinant techniques.

Moreover, by utilization of such recombinant techniques, one skilled in the art may prepare derivatives of native domain 3 such as by site-directed mutagenesis of the relevant DNA, wherein the native amino acid sequence is modified by resultant single or multiple amino acid substitutions, deletions or additions. All such modifications resulting in a derivative domain 3 polypeptide are included within the scope of the invention provided the molecule substantially retains the ability to inhibit HK and LK cell binding, and/or inhibit thrombin-induced cell activation and thereby is able to influence the rate of kallikrein cleavage of those proteins on cells and the release of bradykinin.

Conservative amino acid changes may be made which do not alter the biological function of the domain 3 polypeptide. For instance, 1 polar amino acid, such as glycine, may be substituted for another polar amino acid; or one acidic amino acid, such as aspartic acid, may be substituted for another acidic amino acid, such as glutamic acid; or a basic amino acid, such as lysine, arginine or histidine, may be substituted for another basic amino acid; or a non-polar amino acid, such as alanine, leucine, or isoleucine, may be substituted for another, non-polar amino acid.

Accordingly, a polypeptide having an amino acid sequence "corresponding" to domain 3 embraces not only native domain 3 but also any analog or fragment thereof which retains the essential biological activity of domain 3. Analogs include any polypeptide having an amino acid sequence substantially similar to that of native D3 in which one or more amino acids have been substituted or inserted in the native sequence. Fragments include polypeptides of a length less than the full length of native domain 3. The practice of the present invention is thus not limited to polypeptides of the same length of the native domain 3, but also includes such fragments of the native sequence, provided they substantially retain the ability to block HK and LK binding to cells and increase the bradykinin-release potentiating activity of native domain 3, and/or substantially retain the ability to block thrombin binding to cells, principally platelets and endothelial cells, to inhibit thrombin-induced activation of those cells.

Preferably, the domain 3 polypeptides employed in the present invention, retain a substantial sequence homology with the amino acid sequence of native domain 3. The sequence homology is preferably at least about 50%, more preferably at least about 80%, most preferably at least about 90%.

Whether an analog or fragment retains a particular biological activity of the native 21 kDa trypsin-cleavage fragment may be determined by those skilled in the art by following the experimental protocols set forth hereinafter.

I. Isolation of Kininogen Heavy Chain Domain 3

A. Preparation of Low Molecular Weight Kininogen

LK was purified as follows by a modified procedure of Johnson et al., *Thromb. Res.* 48, 187 (1987) and Müller-Esterl et al., *Methods Enzymol* 163, 240 (1987). All operations were carried out in plastic material since glass activates the enzymes of this system. All reagents were purchased from the Sigma Chemical Co., St. Louis, Mo.

LK was isolated from fresh human plasma in the presence of proteinase inhibitors. Four hundred and fifty ml of blood were collected and immediately mixed with 50 ml of 3.8% sodium citrate, containing 37.5 mg soybean trypsin inhibitor, 2.5 g glucose, 150 mg polybrene, 10 mM EDTA, and 10 mM benzamidine. Following centrifugation at 1,000×g at room temperature for 25 min, the plasma was removed and was treated with diisopropylfluorophosphate (DFP) (2 mM, final concentration). The DFP-treated plasma was then applied to a 3.5 cm×20 column of carboxymethyl(CM)-papain-SEPHAROSE 2B equilibrated in 50 mM phosphate buffer containing 1M NaCl, 1 mM benzamidine-HCl, 1 mM of EDTA, and 0.01% (w/v) $NaN_3$, pH 7.5. The CM-papain-SEPHAROSE 2B column was prepared by the procedure of Anastasi et al., *Biochem J.* 211, 129 (1983), and Gournaris et al., *Biochem J.* 221, 445 (1984). After washing the columns with buffer until the $A_{280}$ was below 0.05, the kininogens bound to the column were eluted with the same buffer with the pH adjusted to 11.5. Five ml fractions were collected in plastic tubes containing 1 ml of 1.0M $KH_2PO_4$ to bring the final pH to 7.0. The $A_{280}$ peak which contained the kininogens was collected and assayed by counter-immunoelectrophoresis using a polyclonal antiserum to human kininogen heavy and light chains made in goats (Schmaier et al., *Thromb. Res.* 33, 51 (1984)). The fractions with antigenic activity were combined and dialyzed against 4 liters of 20 mM Tris-HCl containing 1 mM benzamidine, 1 mM EDTA, and 0.01% $NaN_3$ (w/v), pH 7.5 overnight at 4° C. This preparation of material contained all plasma kininogens, LK and HK.

Additional procedures were performed to separate LK from HK. Since HK has a region on its domain 5 which has the ability to bind to anionic surfaces, kaolin adsorption may be used to separate HK from LK. The pooled and concentrated kininogens eluted from the CM-papain affinity column were treated with various concentrations of kaolin for variable periods of time. Kaolin in various concentrations [(0.25 to 8%) w/v] was mixed with the kininogen preparations (protein content 0.5 mg/ml) by intermittantly vortexing the suspensions at 37° C. for 10 min. In other experiments, the same kininogen preparations were mixed with 1% kaolin (w/v) and incubated at 37° C. from 10 to 60 min. When the concentration of kaolin was increased up to 0.5%, the 120 kDa band was completely removed. Removal of the 120 kDa band correlated with the loss of HK procoagulant activity. In further studies, the 66 kDa band was also found to be decreased after adsorption with higher concentrations of kaolin (≧6% kaolin). These studies indicate that the optimal concentration of kaolin for adsorption of the 120 kDa band (HK) was 0.5% to 1%. Alternatively, studies were also performed to determine if the incubation time with kaolin influenced HK's adsorption by the surface. Within 10 min, all of the 120 kDa band was adsorbed by 1% kaolin. Increasing the incubation time from 10 to 60 min did not increase the extent of kininogen adsorption. After the incubations, HK associated with the kaolin was removed by centrifugation of the sample at 3,000 g× for 20 min. The supernatant containing the unbound kininogen was then dialyzed against 10 mM Tris-HCl overnight at 4° C. After concentrating the residual kininogen by dialysis against polyethylene glycol, $M_r$ 20,000, the final preparations were re-gel filtered on a SEPHADEX G-75 column (1.5cm×150) to characterize their homogeneity. The kininogen not adsorbed to kaolin after gel filtration was characterized not to contain any residual HK procoagulant activity. On silver stained sodium dodecylsulfate polyacrylamide gel electrophoresis (SDS-PAGE), the unadsorbed kininogen had a molecular weight of 64 kDa. Furthermore, an enzyme-linked immunosorbent assay using the anti-light chain monoclonal antibody C11C1 from hybridoma ATCC HB-8964 (U.S. Pat. No. 4,908,431) was performed on the final kininogen preparation. The preparation was found not to contain any antigen that this antibody reacted with. These studies indicate that LK has been purified.

B. Low Molecular Weight Kininogen Trypsin Digestion

Purified LK was treated by limited digestion with trypsin (EC 3.4.21.4 from bovine pancreas) according to the method of Salvesen et al., *Biochem. J.* 234, 429 (1986). Briefly, 15 mg of purified LK was treated with 40 μg trypsin in 8 ml of 50 mM Tris-HCl, 200 mM NaCl, pH 8.0. After incubation for 40 min at 37° C., the digestion was stopped by the addition of DFP (2 mM final concentration). The digest was then loaded on a column (1.5 cm×150) of SEPHADEX G-75 in 50 mM-Tris/HCl, 0.15M NaCl pH 7.5, which ran overnight at 4° C. at a flow rate of 15 ml/h. Fractions (3 ml) were collected and the absorbance at 280 nm was measured. Tryptic digest proteins of 21 and 44 kDa were identified on silver-stained SDS-PAGE. The gel-filtered 21 kDa protein is domain 3. The purity of this material was assessed by the silver-stained SDS-PAGE, by immunochemical specificity using antibodies uniquely directed to D3 (see below), and by N-terminal amino acid sequence. The 44 kDa fragment was further digested with chymotrypsin to isolate 16 and 25 kDa fragments comprising kininogen heavy chain domains 1 and 2, respectively.

C. Identification of Kininogen Heavy Chain Domain 3

The 21 kDa tryptic fragment was identified by monoclonal antibodies which react with domain 3. The antibodies were prepared according to the hybridoma technique essentially as described by Kohler & Milstein, *Nature* 256, 493–497 (1975), using high molecular weight kininogen as the immunogen.

II. Localization of Kininogen Cell-Binding Site to Heavy Chain Domain 3

Various experiments were conducted as follows to confirm that the human kininogen heavy chain domain 3 contains the site through which kininogen binds to cells.

A. Radiolabelling

HK and D3 were radioiodinated by the Iodogen method using the same procedure as previously published for HK (Fraker and Speck, *Biochem. Biophys. Res. Commun*, 80, 849 (1978)). The specific radioactivity ranged from 4.5 to 10.2 μCi/μg protein. Greater than 95% of the radioactivity was precipitated by 10% trichloroacetic acid and >85% of the protein molecules were iodinated. The percentage of iodinated HK molecules in each batch of the radiolabelled material was determined by the ratio of atoms of iodide incorporated into the protein and the number of molecules of HK in the radiolabelled preparation. All batches of $^{125}$I-HK were quantitated for antigen concentration by single radial immunodiffusion.

B. Cell-binding Protocol

All binding experiments described hereinafter were performed with gel-filtered platelets placed into polypropylene tubes, diluted with Hepes-Tyrode's buffer and additions, to a final concentration of 2×10 platelets/ml. Incubations were performed at 37° C. for specified times with various additions. After incubation, 50 μl aliquots were removed in triplicate for each experimental point and placed in polypropylene microcentrifuge tubes with an extended tip containing 200 μl of an oil mixture which consisted of 1 part Apiezon A oil to 9 parts N-butylphthalate (Gustafson et al., *J. Clin. Invest.* 78, 810 (1986)), and centrifuged at room temperature for 2 min. at 12,000×g in a microcentrifuge (Model E, Beckman Instruments, Palo Alto, Calif.). The supernatant was removed, and the tips were amputated. The radioactivity present in the cell pellet was determined with an LKB Rack Gamma Counter (LKB Instruments,. Inc., Gaithersburg, Md.). Nonspecific binding was measured in the presence of a 50- to 100-fold molar excess unlabelled HK or domain 3.

Determination of the amount of bound radioligand was based upon its specific radioactivity and expressed as nanograms bound/$10^8$ platelets per ml or converted to nM or pM bound. The competition inhibition binding data was analyzed using a BASIC program that fits data to a four-parameter logistic function (Canellas and Karu, *J. Immunol. Methods* 47, 375 (1981)), to determine the 50% inhibitory concentration ($IC_{50}$). Inhibition constants were calculated from the $IC_{50}$ values using the technique of Müller, *Meth. Enzymol.* 92, 589 (1983). Previously published studies from our laboratory indicate that the calculated $K_i$ determined from the $IC_{50}$ data are the same as the $K_d$ determined by direct binding studies when the experiments are performed under equilibrium conditions. $^{125}$I-LK domain 3 concentration-dependent binding experiments were analyzed graphically according to the methods of Scatchard, *Ann. N.Y. Acad. Sci.* 51, 660 (1949). In these experiments, total binding was the concentration of added radioligand bound in the presence of 50 μM zinc; nonspecific binding was the concentration of added radioligand bound in the presence of a 100-fold molar excess unlabelled ligand or in the absence of added zinc. Specific binding was calculated by subtracting nonspecific binding from total binding.

In order to prepare human umbilical vein endothelial cells for binding studies (HUVEC), these cells were grown to confluence (4×10$^4$ cells/per well), were cooled to 4° C. on ice for 30 min. and then washed three times in Hepes-Tyrode's buffer containing 50 μM ZnCl$_2$. After washing, the cells were incubated at 4° C. for various periods of time with $^{125}$I-HK (10 nM) in the presence or absence of unlabelled HK or a purified domain from LK's heavy chain. After washing each well eight times with the Hepes-Tyrode's buffer, 50 μl of 1N NaOH was added to each well for 30 min. to remove the cells from the plate. Cell-associated radioactivity was determined by counting the contents of each well in a gamma counter. Total binding was determined by measuring the amount of $^{125}$I-HK bound to the cells in the absence of any competitor and nonspecific binding was determined by the amount of $^{125}$I-HK binding to HUVEC in the presence of 50-fold molar excess of unlabelled HK.

C. Localization of Cell-Binding Site to Domain 3

(i) Domain 3 Inhibition of $^{125}$I-HK Binding to Platelets

Figure 2:
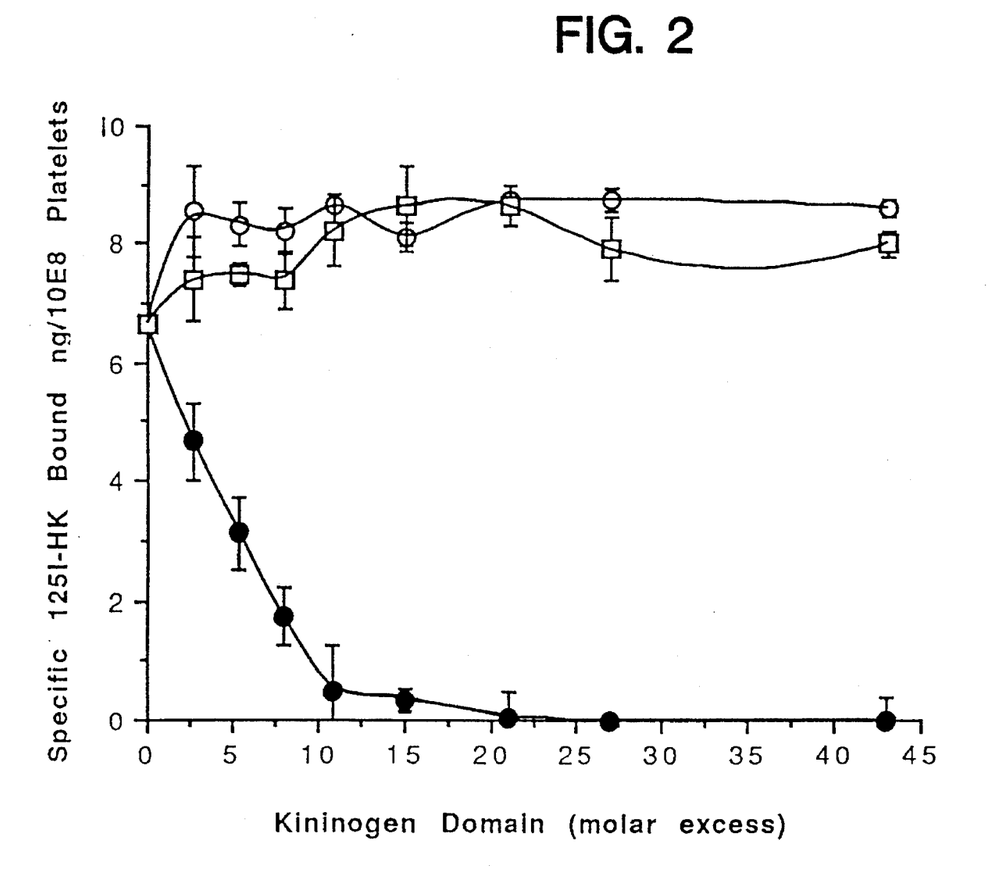
FIG. 2 is a competition inhibition binding study of $^{125}$I-HK binding to platelets by purified domains of LK. Gel-filtered platelets ($2.0\times10^8$/ml) in Hepes-Tyrode's buffer were incubated for 20 min. with 10 nM $^{125}$I-HK in the presence of 50 μM $Zn^{2+}$ and increasing concentration of unlabelled LK domains (D1 o; D2 □; D3 ●). Nonspecific binding was determined by adding a 50-fold molar excess of unlabelled HK. Specific binding was calculated by subtracting nonspecific binding from the total $^{125}$I-HK binding. The Figure is the mean ±SD of the data derived from four experiments.

To determine the domain on kininogens' heavy chain that contains its binding site to platelets, washed platelets were incubated for 20 minutes with 10 nM $^{125}$I-HK and increasing concentration of the purified, unlabelled domains in the presence of 50 μM $Zn^{2+}$. Specific $^{125}$I-HK binding to platelets was completely inhibited by 25-fold molar excess domain 3, but not domain 1 or domain 2 (FIG. 2, ●). Using the mean value determined from four experiments, D3 inhibited $^{125}$I-HK binding to platelets with an $IC_{50}$ of 50 nM, which calculates to an apparent $K_i$ of 15 nM.

(ii) Specificity of $^{125}$I-Domain 3 Binding to Platelets

Figure 3:
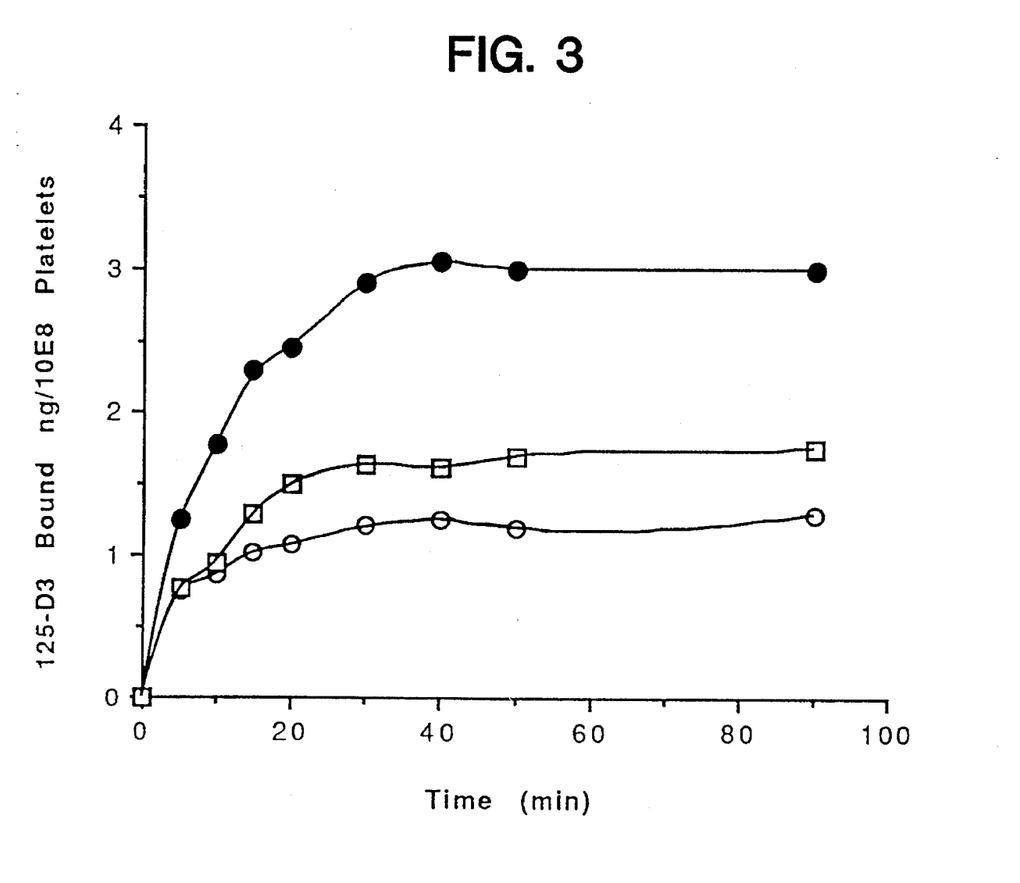

Since indirect binding studies showed that $^{125}$I-HK binding to platelets was inhibited by D3, direct $^{125}$I-D3 platelet-binding studies were performed. Washed platelets were incubated for 5 to 90 minutes at 37° C. with 30 nM $^{125}$I-D3 at the presence of 50 μM $Zn^{2+}$ without any competitor (FIG. 3 o). At each time point, samples were removed and the bound $^{125}$I-D3 was separated from unbound by centrifugation through an oil gradient. Nonspecific binding was measured concomitantly using replicate incubants containing a 35-fold molar excess of unlabelled D3 (FIG. 3, o) or 200-fold molar excess intact HK (FIG. 4, □) in the presence of 50 μM zinc. The data plotted are the mean of three experiments. At any time assayed from 5 to 90 min., there was a significant increase in specific $^{125}$I-D3 binding to platelets. Maximum specific binding was reached in an approximately 30–40 min. Both unlabelled D3 (35-fold molar excess) or HK (200-fold molar excess) were efficient competitors to $^{125}$I-D3 binding to platelets.

Further studies were performed to study the specificity of $^{125}$I-D3 binding to platelets by determining whether a number of related or unrelated proteins block $^{125}$I-D3 binding to platelets. Binding of $^{125}$I-D3 was not inhibited by a 50-fold molar excess of C1s, C1 inhibitor, prekallikrein, or factor XII. Only a 25-fold molar excess of unlabeled D3 or ≧50-fold molar excess of HK inhibited $^{125}$I-D3 binding to platelets.

(iii) Domain 3 Inhibition of $^{125}$I-Domain 3 Binding to Platelets

Figure 4:
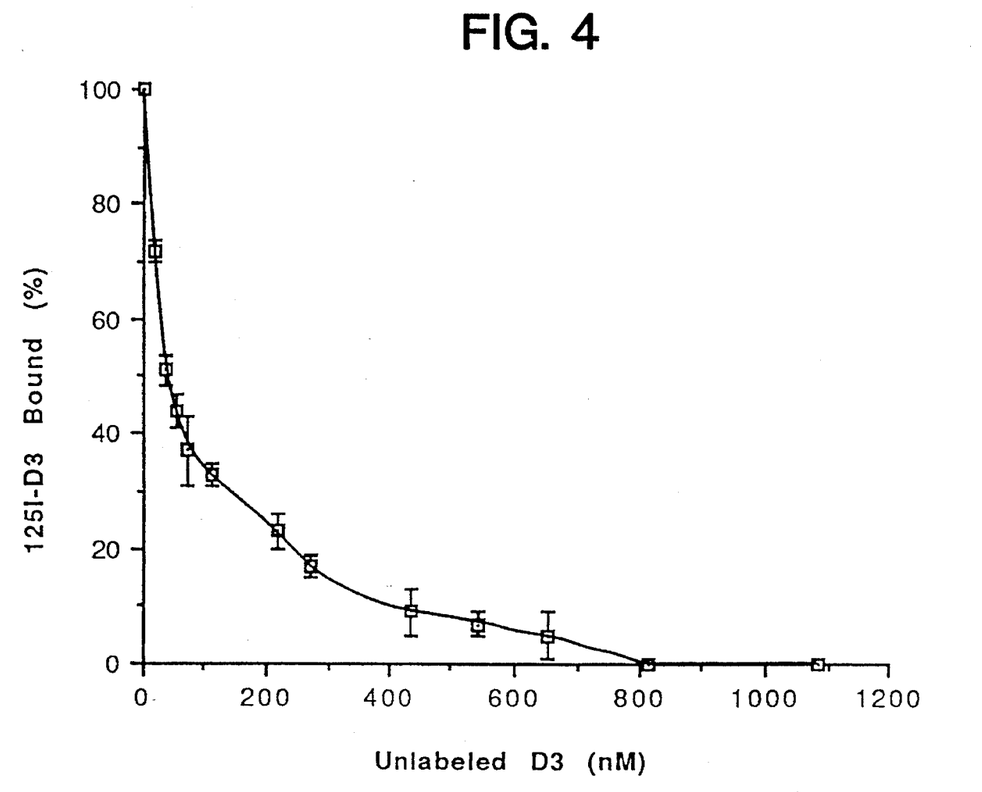

The specificity of $^{125}$I-D3 binding to platelets was also assessed by examining the effect of increasing concentrations of unlabelled D3 on the binding of $^{125}$I-D3. $^{125}$I-D3 (30 nM) was incubated with washed platelets in Hepes-Tyrode's buffer containing 50 μM $Zn^{2+}$ for 20 min. at 37° C. in the presence of increasing concentrations of unlabelled D3. The results are shown in FIG. 4. Percent specific binding of $^{125}$I-D3 is depicted on the ordinate. The abscissa represents the concentration of the unlabelled D3. Plotting the mean values for each concentration of the unlabelled D3 from three individual experiments, D3 was observed to inhibit $^{125}$I-D3 binding to platelets with an $IC_{50}$ of 69 nM (calculated apparent $K_i$ of 15 nM). These values were in reasonable agreement with the values obtained with D3 inhibition of $^{125}$I-HK binding to platelets (FIG. 2).

The specificity of $^{125}$I-D3 binding to platelets was further studied by comparing the molecular mass of unlabelled D3, radiolabelled D3, and platelet-bound $^{125}$I-D3. This preparation of the purified domain was reactive with a D3-specific monoclonal antibody in immunoblotting. The apparent molecular mass of D3 on immunoblot after SDS-PAGE appeared unchanged when compared to unlabelled D3 silver-stained on SDS-PAGE, $^{125}$I-D3, or the platelet-bound $^{125}$I-D3. These data indicate that the radiolabelled D3 was one species which was not processed when bound to platelets.

Studies were conducted to determine if unlabelled D3 could displace $^{125}$I-D3 already bound to the surface of the platelets. The binding of $^{125}$I-D3 to platelets was fully reversible. When a 35-fold molar excess of unlabelled D3 was added at 10, 30 and 50 min. after binding of $^{125}$I-D3 to platelets, the level of the bound radioligand decreased rapidly to the level of nonspecific binding.

(iv) Saturability of $^{125}$I-D3 Binding to Platelets

Figure 5A:
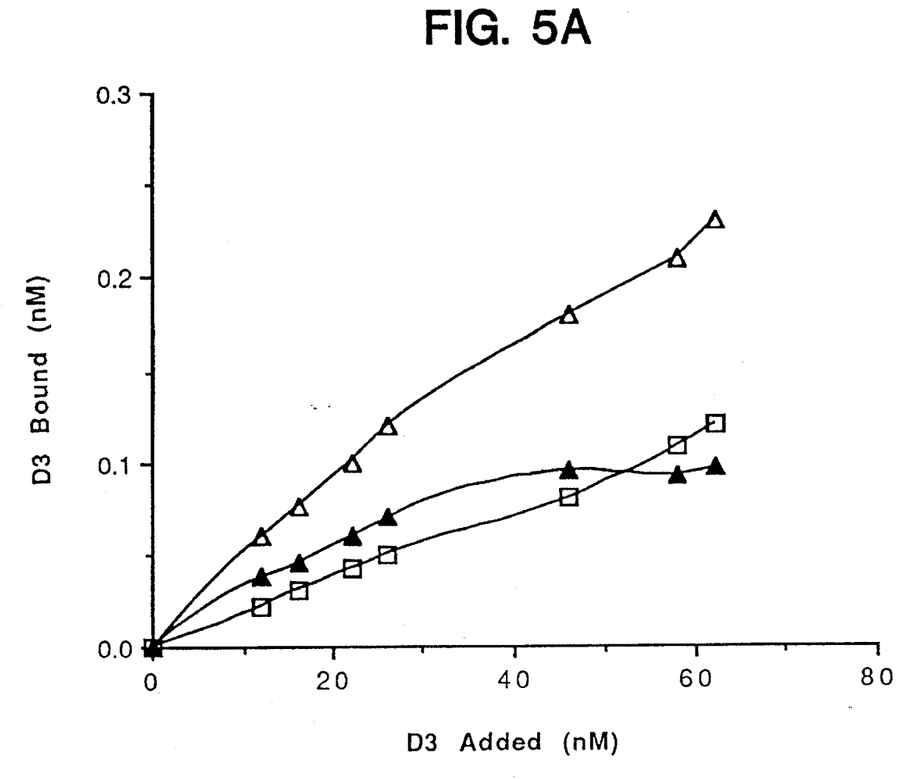
FIGS. 5A and 5B comprise a concentration-dependent binding study of $^{125}$I-D3 to platelets. Gel-filtered platelets in Hepes-Tyrode's buffer were incubated for 20 min. at 37° C. with increasing concentrations of $^{125}$I-D3 in the presence of 50 μM $Zn^{2+}$.
Figure 5B:
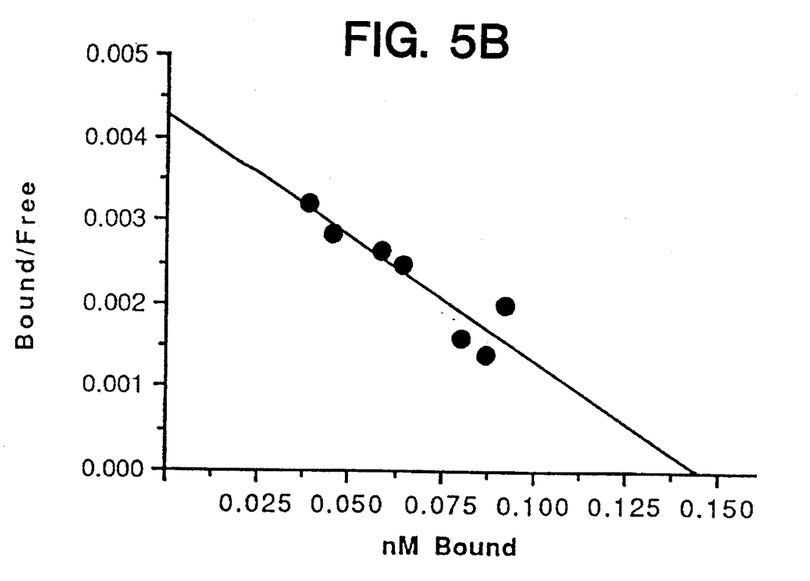

Since $^{125}$I-D3 binding to platelets was specific and reversible, studies were performed to determine the saturability of $^{125}$I-D3 binding to platelets. Gel-fittered platelets in Hepes-Tyrode's buffer were incubated for 20 minutes at 37° C. with increasing concentrations of $^{125}$I-D3 in the presence of 50 μM $Zn^{2+}$. In FIG. 5A, increasing concentrations of $^{125}$I-D3 were added to platelets in the absence or presence of a 35-fold molar excess unlabelled D3. Specific binding (▲) was calculated by subtracting nonspecific binding (□) from total binding (Δ). Nonspecific binding was determined by adding the 35-fold molar excess of unlabelled D3. Specific binding was observed at all concentrations. A plateau of specific binding was observed between 30 and 40 nM added radioligand (FIG. 5A). When these specific binding data were analyzed by the method of Scatchard, supra, a single saturable binding site was found with an apparent Kd of 39 nM±8 and 1227 sites/platelet±404 (n=4) (FIG. 5B).

Figure 6:
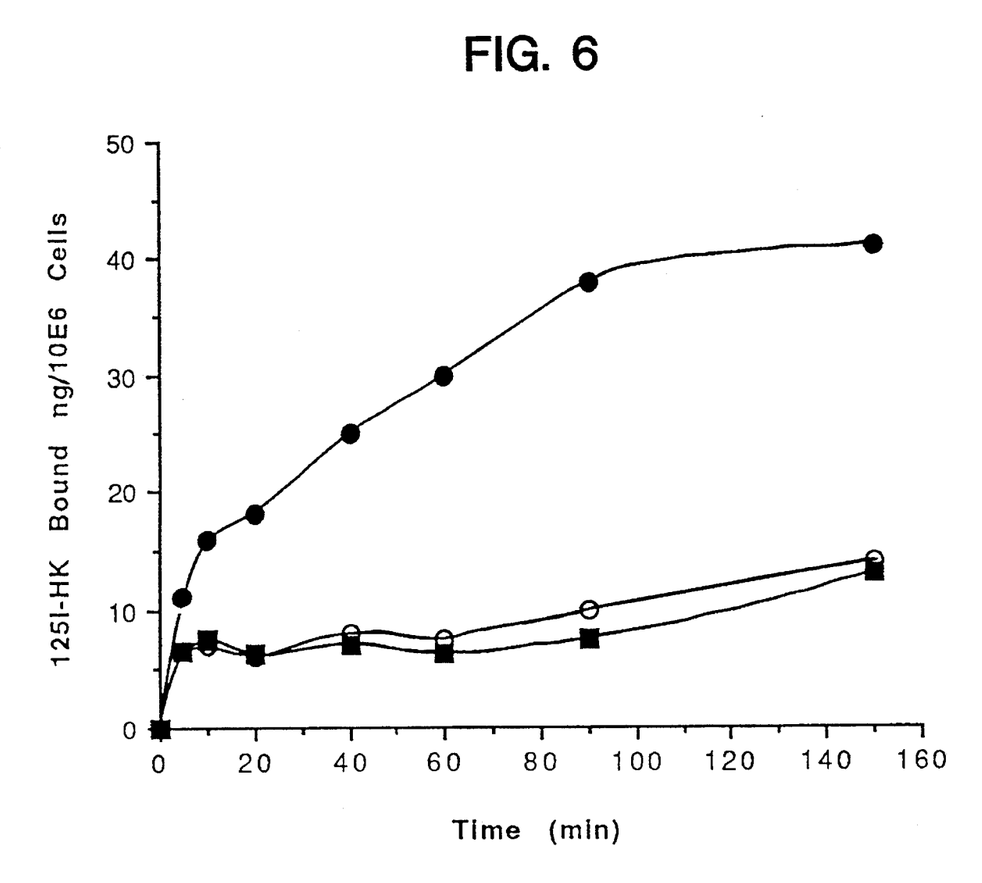
FIG. 6 shows the competition of $^{125}$I-HK binding to human umbilical vein endothelial cells (HUVEC) by unlabelled D3. Confluent monolayers of HUVEC in microtiter plates were washed with Hepes-Tyrode's buffer containing 50 µM $ZnCl_2$, chilled on ice, and incubated with $^{125}$I-HK (10 nM) in the absence or presence of 30-fold molar excess of unlabelled D3 (■) for the indicated length of time. Total binding (●) was determined by measuring the amount of $^{125}$I-HK binding to the cells in the absence of any competitor. Nonspecific binding was determined by measuring the amount of $^{125}$I-HK that binds to the cells in the presence of a 50-fold molar excess of unlabelled HK (○).

In other studies, it was determined that D3 inhibited $^{125}$I-HK binding to human umbilical vein endothelial cells (HUVEC). Confluent monolayers of human umbilical vein endothelial cells in microtiter plates were washed with Hepes-Tyrode's buffer containing 50 μM $ZnCl_2$, chilled on ice, and incubated with $^{125}$I-HK (10 nM) in the absence or presence of 30-fold molar excess of unlabelled D3 (FIG. 6, ■) for the indicated time period. Total binding (FIG. 6, ●) was determined by measuring the amount of $^{125}$I-HK binding to cells in the absence of any competitor. Nonspecific binding was determined by measuring the amount of $^{125}$I-HK that binds to the cells in the presence of a 50-fold molar excess of unlabelled HK (FIG. 6, o). Binding of $^{125}$I-HK (10 nM) to HUVEC was inhibited by 35-fold molar excess of unlabelled D3. These data indicate that D3 is the binding site for other cells which bind kininogen, not just platelets.

III. Characterization Of The Influence Of Human Kininogen's Platelet Binding On Bradykinin Liberation A. Platelet Protection of High Molecular Weight Kininogen from Kallikrein Cleavage A study was performed to determine if platelet-bound HK was a substrate for plasma and tissue kallikreins. All samples described hereafter were reduced with 5% β-mercaptoethanol and boiling, and applied to SDS-PAGE. $^{125}$I-HK was incubated with plasma kallikrein at a concentration of 0.35 μg/ml, at 37° C. for from 0 to 120 minutes. The kallikrein concentration of 0.35 μg/ml is about 1% of activated prekallikrein in plasma. The radioligand was rapidly cleaved within 1 min. into a 64 kDa heavy chain and a 56 kDa light chain, as determined by SDS-PAGE. Less than 6% of the total HK remained intact at 120 kDa. Alternatively, when the same concentration of $^{125}$I-HK was bound to platelets and incubated with the same concentration of plasma kallikrein, the rate of cleavage of the platelet-bound HK was retarded when compared to the fluid phase incubation. Approximately 30% of the radioligand remained intact at 120 kDa after 1 min. Full cleavage of the 120 kDa $^{125}$I-HK was completed in the fluid phase by 10 min. but at even 120 min., some of the platelet-bound $^{125}$I-HK remained uncleaved. The protection from cleavage only occurred with platelet-bound HK because any $^{125}$I-HK that eluted from the platelets during the incubation was cleaved almost as rapidly as the kininogen incubated in solution with the plasma kallikrein.

Similar findings occurred when recombinant human urinary kallikrein was used as the kininogenase. In a soluble cleavage reaction, intact 120 kDa $^{125}$I-HK was rapidly cleaved by human urinary kallikrein (0.7 μg/ml) into 64, 56 and 45 kDa bands. At 10 min., only 5% of the radioligand remained intact. After 10 min. incubation, platelet-bound $^{125}$I-HK was less cleaved since 32% of the radioactivity remained at 120 kDa. Even at 120 min. incubation, 19% of the platelet-bound $^{125}$I-HK was intact (120 kDa) and seemed to be resistant to cleavage by human urinary kallikrein. In a control incubation for 2 h at 37° C., $^{125}$I-HK bound to platelets and not treated with kallikrein did not become cleaved. The protection of platelet-bound HK from kallikrein cleavage only occurred with the radiolabelled HK that remained platelet-bound. $^{125}$I-HK that eluted from the platelets was rapidly cleaved, within 10 min. by human urinary kallikrein since only 7% of the protein remained at 120 kDa.

B. Bradykinin Release in the Absence of Platelet Protection of High Molecular Weight Kininogen Additional studies were performed to confirm that the cleavage of radiolabelled HK is associated with bradykinin liberation. HK (100 μg) was cleaved with purified plasma kallikrein (4 μg) or purified recombinant human urinary kallikrein (4 μg) and applied to SDS-PAGE. Another aliquot was electroblotted onto nitrocellulose and immunoblotted with an antibody to the heavy chain and light chain of kininogen, or an antibody to bradykinin. Both plasma and urinary kallikrein cleaved HK from an intact band at 120 kDa to a thick band that extends from 64 to 56 kDa. Another faint band at 46 kDa was also seen in the cleavage experiment with plasma kallikrein. On immunoblot of these same kallikrein-treated specimens, mostly cleaved kininogen was seen, although a small quantity of intact 120 kDa HK was detected using an antibody that recognizes both the heavy and light chains of HK. However, when an antibody to bradykinin, which recognizes on Western blot kinin contained in intact kininogen, was applied to the immunoblot, only the intact HK starting material was detected. Neither of the kallikrein-cleaved HKs was detected with the antibradykinin antibody. This latter finding indicated that the cleaved kininogen is bradykinin-free. Since platelet-bound HK is protected from kallikrein cleavage, i.e., it is cleaved at a slower rate than non-bound HK, and since HK cleaved by kallikrein has been shown to liberate bradykinin, the data taken together indicate that the binding of HK to platelets modulates the rate by which bradykinin is liberated from the pool of kininogen. Non-bound HK delivers more bradykinin at a faster rate to lower blood pressure than platelet-bound HK. Thus, administration of a polypeptide corresponding to D3, which effectively blocks kininogen binding to cells as shown above, will deliver up more bradykinin to the circulation to influence blood pressure.

IV. Inhibition of Thrombin-induced Platelet Activation by Kininogen Heavy Chain Domain 3

The binding of thrombin to its receptor on the platelet surface is an essential requirement for this plasma protease to elicit platelet activation (aggregation and secretion).

The following studies demonstrate that purified polypeptides corresponding to domain 3 are useful as inhibitors of thrombin-induced platelet activation. Inhibition of platelet activation is manifested by a decrease in secretion of platelet granule contents and a decrease in aggregation. The ability of domain 3 to inhibit platelet activation is not the result of any direct alteration of thrombin. Domain 3 does not inhibit the proteolytic activity of thrombin. Rather, D3 inhibits thrombin activation of platelets by inhibiting that enzyme from binding to platelets. Thus, D3 is useful as a selective antithrombotic agent in that it effectively inhibits only thrombin-induced activation of platelets but leaves intact the ability of platelets to respond to stimulation by other physiologic platelet activators such as collagen, adenosine triphosphate, epinephrine and platelet activating factor. Furthermore, since D3 functions by blocking thrombin's binding to platelets, the polypeptide prevents thrombin from activating platelets but leaves thrombin's intrinsic enzyme activity intact. Specifically, administration of domain 3 polypeptide should have no effect on thrombin's ability to cleave its principal substrate fibrinogen into the clot-forming protein fibrin. Therefore, D3 is useful as an antithrombotic agent for inhibiting platelet activation and perhaps activation of other cells of the intravascular compartment, without causing the bleeding complications of other antithrombotic agents.

A. Domain 3 Inhibition of Thrombin Binding to Platelets

Figure 7:
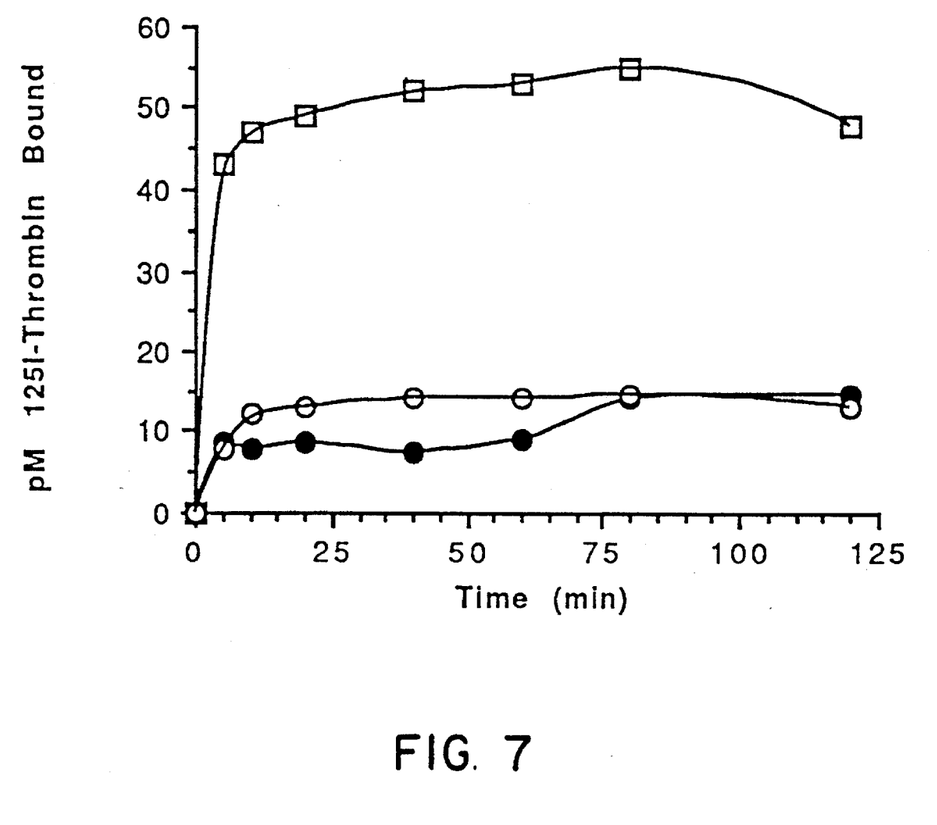

Gel-filtered platelets (2×10$^8$/ml) in Hepes-Tyrode's buffer containing 50 μM ZnCl$_2$ and 2 mM CaCl$_2$ were incubated for 5–120 min. at 37° C. with 1 nM $^{125}$I-α-thrombin (IIa) alone (□) or in the presence of 200 nM HK (●) or 200 nM D3 (○). The data plotted in FIG. 7 are the mean of two independent experiments. Both 200 nM HK or D3 were able to inhibit $^{125}$I-α-thrombin binding. platelets. Thus, this study indicates that D3 contains the site on the kininogens responsible for inhibiting thrombin binding to platelets.

B. Domain 3 Inhibition of Thrombin-induced Platelet Aggregation

Figure 8:
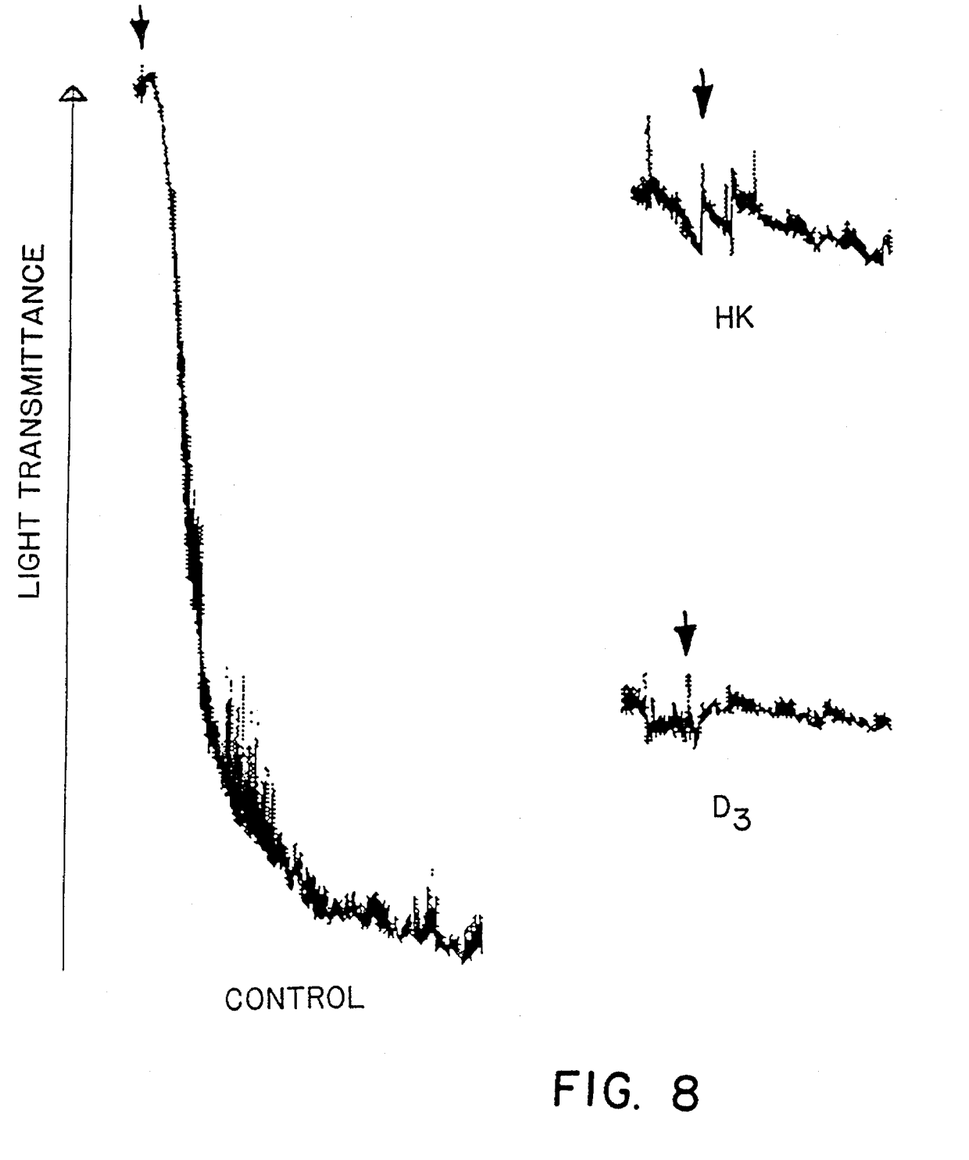

Gel-filtered platelets (2.0×10$^8$/ml) in Hepes-Tyrode's buffer were treated with 1 μM HK or D3 immediately before the introduction of the agonist, human α-thrombin (0.125 U/ml), which is indicated by the arrows. Platelet aggregation was measured in an aggregometer (Chronolog Corp., Havertown, Pa.) for 5 min. after the introduction of the agonist. Control platelets received an identical volume of buffer. Platelet aggregation was measured in arbitrary units as the initial rate of change in light transmission in the first minute after the introduction of the agonist. The results are shown in FIG. 8, which is a representative experiment of three experiments performed with different platelet donors and different batches of HK and D3. The batches were carefully dialyzed to remove any trace of inhibitors necessary in their preparation.

C. Domain 3 Inhibition of Thrombin-induced Secretion of Platelet Granule Contents The following experiment demonstrates that domain 3 polypeptide decreases platelet secretion of the platelet-dense granule marker [$^{14}$C]5-hydroxytryptamine.

Fresh platelet-rich plasmas were incubated with [$^{14}$C]5-hydroxytryptramine (10 ml:1 μl v/v) for 30 min at 37° C. and then treated with imipramine (2 nM). The treated plasmas were subjected to gel filtration. (The purified HK used in the experiment was dialyzed extensively against 0.01 PBS, pH 7.4). The washed platelets (3×10$^8$/ml of final concentration labeled with [$^{14}$C]5-hydroxytryptamine were incubated with increasing concentrations of HK or D3 at 37° C. for 1–5 min. in a cuvette of an aggregometer (Chronolog Corp., Havertown, Pa.) with stirring. α-Thrombin (0.125 Units/ml final concentration) was then added to initiate platelet activation. At precisely 1 min. from the introduction of the stimulus, 200 μl from each sample were removed and placed into Eppendorf tube containing 50 μl of a 135 mM formaldehyde, 5 mM EDTA solution and centrifuged at 12,000×g. After centrifugation the tubes were placed on ice until an aliquot of the supernatant was assayed for secreted [$^{14}$C]5-hydroxytryptamine. Percent secretion was determined by the ratio of the supernatant of the agonist treated sample to the supernatant of the platelet lysate after the value of the background radioactivity was subtracted from both. D3, like HK, decreased the ability of thrombin to induce secretion of the platelet-dense granule markers [$^{14}$C]5-hydroxytryptamine in concentration-dependent fashion, although D3 (IC50=200–300 nM) is a less potent inhibitor than HK (IC50=30–50 nM).

V. Therapeutic Administration of Kininogen Heavy Chain

Purified polypeptide corresponding to domain 3 may be administered in any circumstance where blood pressure reduction and/or inhibition of thrombin-induced platelet activation is sought. The polypeptide may be administered by any convenient means which will result in delivery into the bloodstream in substantial amount. Intravenous administration is presently contemplated as the preferred administration route, although intranasal administration may also be utilized. Since domain 3 is soluble in water, it may therefore be effectively administered in solution. Since the plasmic concentration of HK and LK are 0.6 and 2.4 μM respectively, all intravascular in vivo binding sites for kininogen would be expected to be saturated. Thus, infusion of domain 3 polypeptide at concentrations approaching 5 μM would be sufficient to block cell-binding of kininogen to facilitate its cleavage by kallikrein, thereby resulting in bradykinin release. The same concentration would be effective to inhibit the cell binding of thrombin, to inhibit thrombin-induced platelet activation, and to inhibit thrombin induced endothelial and other cell activation.

The polypeptide may be administered in a pharmaceutical composition in admixture with a pharmaceutically-acceptable carrier. The pharmaceutical composition may be compounded according to conventional pharmaceutical formulation techniques. The carrier may take a wide variety of forms depending on the form of preparation desired for administration. For a composition to be administered parenterally, the carrier will usually comprise sterile water, although other ingredients to aid solubility or for preservation purposes may be included. Injectable suspension may also be prepared, in which case appropriate liquid carriers, suspending agents and the like may be employed. The preferred parenteral route of administration is intravenous administration.

For intravenous administration, the domain 3 polypeptide may be dissolved in any appropriate intravenous delivery vehicle containing physiologically compatible substances, such as sodium chloride, glycine and the like, having a buffered pH compatible with physiologic conditions. Such intravenous delivery vehicles are known to those skilled in the art.

The amount of polypeptide administered will depend upon the degree of blood pressure modulation or platelet aggregation inhibition desired. While infusion of sufficient domain 3 polypeptide to obtain a 5 μM intravascular concentration may be advantageously utilized, more or less polypeptide may be administered as needed. The actual amount of polypeptide administered to achieve the desired intravascular concentration is readily determinable by those skilled in the art by routine methods.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method for increasing vascular bradykinin release comprising administering to an individual in need of such treatment an effective amount of a polypeptide which inhibits the cell binding of human kininogen, wherein said polypeptide is selected from the group consisting of:

(A) the about 21 kDa native trypsin-cleavage fragment of human kininogen heavy chain, (B) fragment of said native trypsin-cleavage fragment, and (C) an analog of said native trypsin-cleavage fragment selected from the group consisting of:
  (1) an amino acid deletion analog formed by deleting up to 50% of the amino acids from said native trypsin-cleavage fragment,
  (2) an amino acid insertion analog formed by inserting one or more amino acids into the sequence of amino acids of said native trypsin-cleavage fragment, whereby the number of amino acids of said analog is increased up to 50% beyond the number of amino acids of said native trypsin-cleavage fragment,
  (3) an amino acid addition analog formed by adding one or more amino acids to the amino and/or carboxy terminus of said native trypsin-cleavage fragment, whereby the number of amino acids of said analog is increased up to 50% beyond the number of amino acids of said native trypsin-cleavage fragment, and
  (4) a mixed analog formed by any combination of two or more of the following:
    (a) deleting one or more amino acids from said native trypsin-cleavage fragment,
    (b) inserting one or more amino acids into said native trypsin-cleavage fragment, and
    (c) adding one or more amino acids to the amino and/or carboxy terminus of said native trypsin-cleavage fragment, wherein the total number of amino acids deleted, inserted or added in generating the amino acid sequence of said mixed analog does not exceed a number equal to 50% of the number of amino acids of said native trypsin-cleavage fragment.

2. A method according to claim 1 wherein the total number of amino acids deleted, inserted or added in generating the amino acid sequence of said analog does not exceed a number equal to 20% of the number of amino acids of said native trypsin-cleavage fragment.

3. A method according to claim 1 wherein the total number of amino acids deleted, inserted or added in generating the amino acid sequence of said analog does not exceed a number equal to 10% of the number of amino acids of said native trypsin-cleavage fragment.

4. A method according to claim 1 wherein the polypeptide is the about 21 kDa native trypsin-cleavage fragment of human kininogen heavy chain.

5. A method according to claim 1 wherein the polypeptide is a fragment of said native trypsin-cleavage fragment.

6. A method according to claim 1 wherein the polypeptide is an amino acid deletion or insertion analog wherein the amino acids deleted or inserted comprise a continuous sequence.

7. A method for lowering blood pressure comprising administering to an individual in need of such treatment an effective amount of a polypeptide which inhibits the cell binding of human kininogen, wherein said polypeptide is selected from the group consisting of:

(A) the about 21 kDa native trypsin-cleavage fragment of human kininogen heavy chain, (B) a fragment of said native trypsin-cleavage fragment, and (C) an analog of said native trypsin-cleavage fragment selected from the group consisting of:
  (1) an amino acid deletion analog formed by deleting up to 50% of the amino acids from said native trypsin-cleavage fragment, (2) an amino acid insertion analog formed by inserting one or more amino acids into the sequence of amino acids of said native trypsin-cleavage fragment, whereby the number of amino acids of said analog is increased up to 50% beyond the number of amino acids of said native trypsin-cleavage fragment, (3) an amino acid addition analog formed by adding one or more amino acids to the amino and/or carboxy terminus of said native trypsin-cleavage fragment, whereby the number of amino acids of said analog is increased up to 50% beyond the number of amino acids of said native trypsin-cleavage fragment, and (4) a mixed analog formed by any combination of two or more of the following:
  (a) deleting one or more amino acids from said native trypsin-cleavage fragment,
  (b) inserting one or more amino acids into said native trypsin-cleavage fragment, and
  (c) adding one or more amino acids to the amino and/or carboxy terminus of said native trypsin-cleavage fragment, wherein the total number of amino acids deleted, inserted or added in generating the amino acid sequence of said mixed analog does not exceed a number equal to 50% of the number of amino acids of said native trypsin-cleavage fragment.

8. A method according to claim 7 wherein the total number of amino acids deleted, inserted or added in generating the amino acid sequence of said analog does not exceed a number equal to 20% of the number of amino acids of said native trypsin-cleavage fragment.

9. A method according to claim 7 wherein the total number of amino acids deleted, inserted or added in generating the amino acid sequence of said analog does not exceed a number equal to 10% of the number of amino acids in said native trypsin-cleavage fragment.

10. A method according to claim 7 wherein the polypeptide is the about 21 kDa native trypsin-cleavage fragment of human kininogen heavy chain.

11. A method according to claim 7 wherein the polypeptide is a fragment of said native trypsin-cleavage fragment.

12. A method according to claim 7 wherein the polypeptide is an amino acid deletion or insertion analog wherein the amino acids deleted or inserted comprise a continuous sequence.

13. A method for inhibiting thrombin-induced platelet or other cell activation comprising administering to an individual in need of such treatment an effective mount of a polypeptide which inhibits thrombin binding to platelets or other cells, wherein said polypeptide is selected from the group consisting of:

(A) the about 21 kDa native trypsin-cleavage fragment of human kininogen heavy chain, (B) a fragment of said native trypsin-cleavage fragment, and (C) an analog of said native trypsin-cleavage fragment selected from the group consisting of:
  (1) an amino acid deletion analog formed by deleting up to 50% of the amino acids from said native trypsin-cleavage fragment,
  (2) an amino acid insertion analog formed by inserting one or more amino acids into the sequence of amino acids of said native trypsin-cleavage fragment, whereby the number of amino acids of said analog is increased up to 50% beyond the number of amino acids of said native trypsin-cleavage fragment,
  (3) an amino acid addition analog formed by adding one or more amino acids to the amino and/or carboxy terminus of said native trypsin-cleavage fragment, whereby the number of amino acids of said analog is increased up to 50% beyond the number of amino acids of said native trypsin-cleavage fragment, and
  (4) a mixed analog formed by any combination of two or more of the following:
    (a) deleting one or more amino acids from said native trypsin-cleavage fragment,
    (b) inserting one or more amino acids into said native trypsin-cleavage fragment, and
    (c) adding one or more amino acids to the amino and/or carboxy terminus of said native trypsin-cleavage fragment, wherein the total number of amino acids deleted, inserted or added in generating the amino acid sequence of said mixed analog does not exceed a number equal to 50% of the number of amino acids of said native trypsin-cleavage fragment.

14. A method according to claim 13 wherein the total number of amino acids deleted, inserted or added in generating the amino acid sequence of said analog does not exceed a number equal to 20% of the number of amino acids of said native trypsin-cleavage fragment.

15. A method according to claim 13 wherein the total number of amino acids deleted, inserted or added in generating the amino acid sequence of said analog does not exceed a number equal to 10% of the number of amino acids of said native trypsin-cleavage fragment.

16. A method according to claim 13 wherein the polypeptide is the about 21 kDa native trypsin-cleavage fragment of human kininogen heavy chain.

17. A method according to claim 13 wherein the polypeptide is a fragment of said trypsin-cleavage fragment.

18. A method according to claim 13 wherein the polypeptide is an amino acid deletion or insertion analog wherein the amino acids deleted or inserted comprise a continuous sequence.

* * * * *

UNITED STATES PATENT AND TRADEMARK OFFICE
CERTIFICATE OF CORRECTION

PATENT NO.    : 5,472,945
DATED         : December 5, 1995
INVENTOR(S)   : Alvin H. Schmeier et al.

It is certified that error appears in the above-identified patent and that said Letters Patent is hereby corrected as shown below:

Column 1,
Insert the following after line 3:
-- Reference to Government Grant
This invention was made, in part, with (U.S.) Government support under Grant Nos. HL 01615 and HL 35553 awarded by the National Institutes of Health. The Government has certain rights in the invention. --.

Signed and Sealed this

Thirtieth Day of March, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( x ) SEQUENCE CHARACTERISTICS:
        ( A ) LENGTH: 117 amino acids
        ( B ) TYPE:AMINO
        ( B ) TYPE:AMINO
        ( C ) TOPOLOGY: linear     ( x i ) SEQUENCE DESCRIPTION: SEQ ID NO:1:

```
Cys  Val  Gly  Cys  Pro  Arg  Asp  Ile  Pro  Thr  Asn  Ser  Pro  Glu  Leu
                    5                        10                       15
Glu  Glu  Thr  Leu  Thr  His  Thr  Ile  Thr  Lys  Leu  Asn  Ala  Glu  Asn
                    20                       25                       30
```

-continued

```
Asn Ala Thr Phe Tyr Phe Lys Ile Asp Asn Val Lys Lys Ala Arg
                    35              40                      45

Val Gln Val Val Ala Gly Lys Lys Tyr Phe Ile Asp Phe Val Ala
                50               55                      60

Arg Glu Thr Thr Cys Ser Lys Glu Ser Asn Glu Glu Leu Thr Glu
                65              70                      75

Ser Cys Glu Thr Lys Lys Leu Gly Gln Ser Leu Asp Cys Asn Ala
                80              85                      90

Glu Val Tyr Val Val Pro Trp Glu Lys Lys Ile Tyr Pro Thr Val
                95              100                     105

Asn Cys Gln Pro Leu Gly Met Ile Ser Leu Met Lys
                110             115
```

( 2 ) INFORMATION FOR SEQ ID NO:2:

( x ) SEQUENCE CHARACTERISTICS:
        ( A ) LENGTH: 5 amino acids
        ( B ) TYPE: amino acid
        ( C ) TOPOLOGY: linear     ( x i ) SEQUENCE DESCRIPTION: SEQ ID NO:2:

```
Gln Val Val Ala Gly
                5
```